(12) United States Patent
Uchida et al.

(10) Patent No.: US 7,410,980 B2
(45) Date of Patent: Aug. 12, 2008

(54) CRYSTALS OF TAXANE DERIVATIVE AND PROCESS FOR THEIR PRODUCTION

(75) Inventors: Seishiro Uchida, Tokyo (JP); Yoshihiro Takayanagi, Tokyo (JP); Makoto Ono, Tokyo (JP)

(73) Assignee: Daiichi Pharmaceutical Co., Ltd., Tokyo (JP)

( * ) Notice: Subject to any disclaimer, the term of this patent is extended or adjusted under 35 U.S.C. 154(b) by 315 days.

(21) Appl. No.: 10/495,437

(22) PCT Filed: Nov. 29, 2002

(86) PCT No.: PCT/JP02/12506

§ 371 (c)(1),
(2), (4) Date: Oct. 26, 2004

(87) PCT Pub. No.: WO03/045953

PCT Pub. Date: Jun. 5, 2003

(65) Prior Publication Data

US 2005/0070579 A1 Mar. 31, 2005

(30) Foreign Application Priority Data

Nov. 29, 2001 (JP) .............................. 2001-363681

(51) Int. Cl.
*A61K 31/443* (2006.01)
*C07D 405/12* (2006.01)
(52) U.S. Cl. .................................... 514/338; 546/283.7
(58) Field of Classification Search .............. 546/283.7; 514/338
See application file for complete search history.

(56) References Cited

U.S. PATENT DOCUMENTS

| 6,075,140 | A | 6/2000 | Terasawa et al. | |
| 6,184,395 | B1 * | 2/2001 | Singh et al. | 549/510 |
| 6,677,456 | B2 | 1/2004 | Soga et al. | |
| 2002/0143178 | A1 | 10/2002 | Soga et al. | |

FOREIGN PATENT DOCUMENTS

| EP | 0826688 | 3/1998 |
| JP | 2000-159757 | 6/2000 |
| WO | 96/33998 | 10/1996 |
| WO | 01/27115 | 4/2001 |
| WO | 02/070512 | 9/2002 |

OTHER PUBLICATIONS

Haleblian et al., "Pharmaceutical Applications, etc.," J of Pharmaceutical Sciences 58 (8), 1969, pp. 911-929.*
Chemical & Engineering News, Feb. 2003, pp. 32-35.*
Brittain et al., "Polymorphism in Pharmaceutical Solids" NY: Marcel Dekker, Inc., 1999, pp. 1-2, 185.*
U.S. Pharmacopia #23, National Formulary #18, 1995, pp. 1843-1844.*
Muzaffar et al., "Polymorphism and Drug Availability", J of Pharmacy (Lahore), 1979, 1(1), 59-66.*
Jain et al., "Polymorphism in Pharmacy", Indian Drugs, 1986, 23 (6), 315-329.*
Wall et al., "Pharmacuetical Applications, etc.," Pharmaceutical Manufacturing, 1986, 33-42.*
Taday et al., "Using Terahertz Pulse, etc.," J of Pharmaceutical Sciences, 92 (4), 2003. 831-838.*
Doelker, Crystalline Modifications, etc., Ann. Pharm. Fr. 2002, 60:161-176 (and english translation pp. 1-39).*
Otsuka et al., "Effect of Polymorphic, etc.," Chem. Pharm. Bull. 47(6):852-856 (1999).*
Ulicky et al., "Comphrehensive Dictionary of Physical Chemistry" NY: PTR Prentice Hall, 1992, p. 21.*
Bernstein et al., "Polymorphism in Molecular Crystals", Oxford: Clarendon Press, 2002, pp. 117, 118, 272 and 273.*
Davidovich et al., "Detection of, etc.," American Pharmaceutical Review, IN: Russell Pub., 2004, 7(1), pp. 10, 12, 14, 16 and 100.*
Caira, "Crystalline Polymorphism of Organic, etc.," Topics in Current Chemistry, 198, Berline Heidelberg: Springer Verlag, 1998, pp. 164-208.*
T. Ishiyama et al., "New Highly Active Taxoids from 9β-dihydrobaccatin-9,10-acetals. Part 2", Bioorganic & Medicinal Chemistry Letter, vol. 12, No. 20, pp. 2815-2819 (2002).

* cited by examiner

*Primary Examiner*—Patricia L Morris
(74) *Attorney, Agent, or Firm*—Greenblum & Bernstein, P.L.C.

(57) ABSTRACT

A crystal of (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate, which has characteristic peaks at diffraction angles (2θ) of 6.2°, 10.3°, 10.7°, 11.4°, and 12.0° in a powder X-ray diffraction pattern, and a method for preparing the aforementioned crystal, which comprises the step of performing crystallization by using an organic solvent selected from the group consisting of a ketone type solvent, a nitrile type solvent, and a mixture thereof, or a mixture of said organic solvent and water.

9 Claims, 6 Drawing Sheets

CRYSTALS OF TAXANE DERIVATIVE AND PROCESS FOR THEIR PRODUCTION

TECHNICAL FIELD

The present invention relates to a novel crystal of a taxane derivative having an antitumor activity and a method for preparing the same.

BACKGROUND ART

Taxol, a compound exhibiting an antitumor activity on the basis of an inhibitory action against depolymerization of microtubules during cell division, is expected to be effective in clinical application as an antitumor agent having a mode of action different from that of conventional antitumor agents. Various kinds of taxol derivatives have so far been disclosed in publications. For example, compounds are disclosed in which a substituent is introduced on the pyridine ring of the side chain at the 13-position to suppress the modification of the compounds by metabolism (International Publication WO 01/27115). In particular, the compound described in Example 7 of the aforementioned international publication [(1S,2S,3R,4S,5R,8R, 9S,10R,13S)-4-acetoxy-2-benzoyloxy-9,10-[(1S)-2-(dimethylamino)ethylidenedioxy]-5,2 0-epoxy-1-hydroxytax-11-en-13-yl (2R,3S)-3-(tert-butoxycarbonylamino)-3-(3-fluoro-2-pyridyl)-2-hydroxypropionate] is hardly metabolized by human liver microsomes and expected as an antitumor agent that can be orally administered.

As for the compound described in Example 7 of the aforementioned international publication, the method for preparation of the compound is also described in Example 9 of the publication, as well as in Example 7. Example 9 describes that the target compound was obtained by "performing an operation similar to that of Step 4 of Example 8". According to that explanation, it is considered that the solvent in the extract of the reaction mixture containing the target compound was evaporated, and the residue was purified by using silica gel chromatography and recrystallized from a mixture of water and ethanol to obtain a solid deduced to be crystals of the target compound. However, no physicochemical value is given in Examples 7 and 9 of the aforementioned international publication that evidences the isolation of the aforementioned compound in the form of a crystal.

DISCLOSURE OF THE INVENTION

The inventors of the present invention repeated numerous experiments according to the method of Example 9 of the aforementioned international publication. As a result, they finally concluded that it was absolutely impossible to obtain a crystalline substance through precipitation even by using a mixture of water and ethanol as a solvent, and that the target substance was unexceptionally obtained as an oil or an amorphous substance. Under the circumstances, the inventors of the present invention conducted various researches to provide the aforementioned compound as a crystalline substance, and they first succeeded in obtaining the crystals of the aforementioned compound by using an organic solvent other than a mixture of water and ethanol. They also found that at least two kinds of polymorphisms of the crystals of the aforementioned compound existed, and a mixture of the two kinds of the crystal forms was obtained depending on conditions such as a type of a solvent for crystallization of the crystals.

As an active ingredient of a medicament, it is desirable to use a crystalline substance, not an amorphous substance, from a viewpoint of stable supply of a product having constant quality and the like, and the crystalline substance is desired to be a single kind of crystal. For these reasons, the inventors of the present invention conducted various researches to obtain a single kind of crystals of the aforementioned compound, and as a result, they found that a crystalline substance of the aforementioned compound consisting of a single kind of crystals was obtainable by using an organic solvent such as acetone, a mixture of acetone and water, or a mixture of acetonitrile and water for crystallization of the aforementioned compound. The present invention was achieved on the basis of these findings.

The present invention thus provides a crystal of (1S,2S,3R, 4S,5R,8R, 9S,10R,13S)-4-acetoxy-2-benzoyloxy-9,10-[(1S)-2-(dimethylamino)ethylidenedioxy]-5,2 0-epoxy-1-hydroxytax-11-en-13-yl (2R,3S)-3-(tert-butoxycarbonylamino)-3-(3-fluoro-2-pyridyl)-2-hydroxypropionate, which has characteristic peaks at diffraction angles (2θ) of 6.2°, 10.3°, 10.7°, 11.4° and 12.0° in a powder X-ray diffraction pattern.

The present invention also provides a method for preparing the aforementioned crystal, which comprises the step of performing crystallization by using an organic solvent selected from the group consisting of a ketone type solvent, a nitrile type solvent, and a mixture thereof, or a mixture of said organic solvent and water. Acetone or acetonitrile can be preferably used as the organic solvent selected from the group consisting of a ketone type solvent, a nitrile type solvent, and a mixture thereof, and a mixture of acetone and water or a mixture of acetonitrile and water can be used as a preferred crystallization solvent. When the aforementioned mixture of an organic solvent and water is used as the solvent, a water content of the aforementioned mixture is preferably 60% by weight or lower, more preferably in the range of 40 to 50% by weight.

According to a particularly preferred embodiment of the aforementioned method, the aforementioned method is provided wherein a mixture of acetone and water that contains water at a ratio of 40 to 50% by weight, or a mixture of acetonitrile and water that contains water at a ratio of 40 to 50% by weight is used as the crystallization solvent in an amount of 20 to 25 parts by weight of the weight of the compound, and the compound is crystallized at a temperature in the range of from 0 to 45° C. and resulting crystals are dried under reduced pressure with stirring at a temperature in the range of from 30 to 60° C.

The present invention further provides an antitumor agent containing the aforementioned crystal as an active ingredient; an antitumor agent in the form of a pharmaceutical composition which contains the aforementioned crystal as an active ingredient and one or more kinds of pharmaceutical additives; use of the aforementioned crystal for the manufacture of the aforementioned antitumor agent; and a method for therapeutic treatment of a tumor, which comprises the step of administering a therapeutically effective amount of the aforementioned crystal to a patient. The present invention also provides the aforementioned crystal to be used for the manufacture of a medicament containing (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate as an active ingredient.

Figure 1:
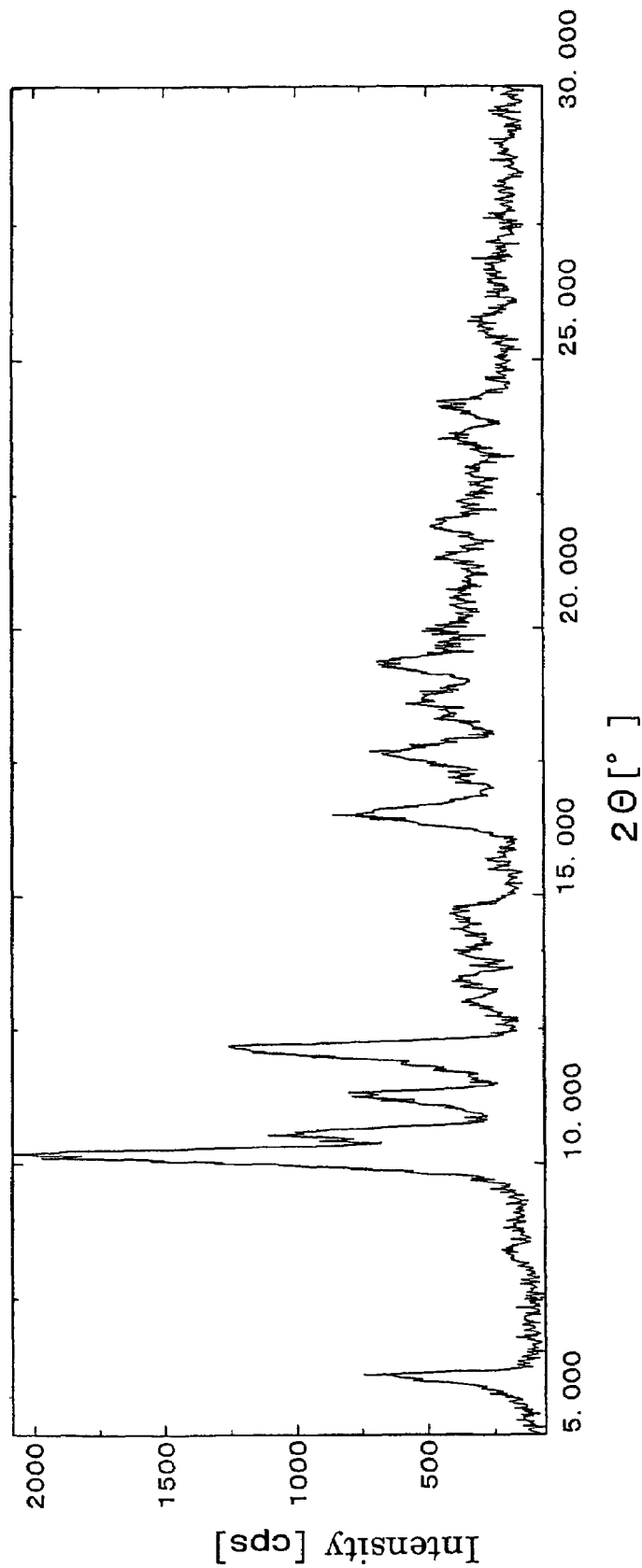
FIG. 1 shows a powder X-ray diffraction pattern of the crystal of the present invention (β crystals).

BEST MODE FOR CARRYING OUT THE INVENTION (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate, a compound represented by the following formula, can be readily produced by those skilled in the art according to the method described in Example 7 of the international publication WO 01/27115.

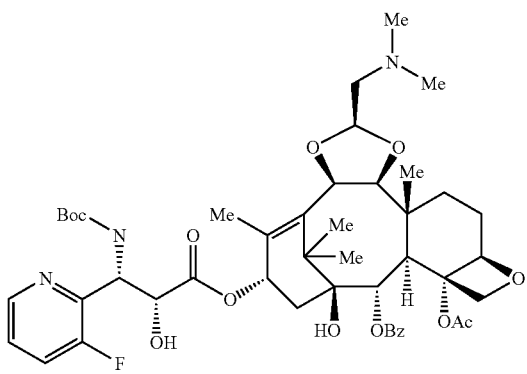

(In the formula, Me represents methyl group, Ac represents acetyl group, Bz represents benzoyl group, and Boc represents tert-butoxycarbonyl group.)

The crystal of the present invention is a crystal of (1S,2S, 3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate which is characterized to have characteristic peaks at diffraction angles (2θ) of 6.2°, 10.3°, 10.7°, 11.4° and 12.0° in a powder X-ray diffraction pattern (this crystal is also referred to as "β crystal" in the specification). Since diffraction angles (2θ) in powder X-ray diffraction generally have an experimental error in a range of less than 5%, each of the aforementioned diffraction angles should be construed to be a numerical range including an allowance of less than 5%. Therefore, crystals having peak diffraction angles in powder X-ray diffraction identical to the above angles with the experimental error of less than 5% crystals, as well as crystals having completely identical peak diffraction angles, fall within the scope of the present invention.

The crystal of the present invention can be produced by subjected the compound prepared according to the method described in Example 7 of the international publication WO 01/27115 to crystallization from a solvent, wherein an organic solvent selected from the group consisting of a ketone type solvent, a nitrile type solvent, and a mixture thereof, or a mixture of the aforementioned organic solvent and water is used. As the ketone type solvent, acetone, methyl ethyl ketone and the like can be used, and acetonitrile and the like can be used as the nitrile type solvent. Among them, acetone and acetonitrile are preferred.

When a mixture of the organic solvent and water is used as the solvent for crystallization, a water content of the aforementioned mixture is preferably 60% by weight or lower, more preferably in the range of 40 to 50% by weight. As the mixture of the organic solvent and water, a mixture of acetone and water and a mixture of acetonitrile and water are preferred. A particularly preferred solvent for crystallization is a mixture of acetone and water that contains water at a ratio of 40 to 50% by weight or a mixture of acetonitrile and water that contains water at a ratio of 40 to 50% by weight. For the crystal precipitation, the aforementioned compound may be directly dissolved in a mixture of acetone and water, a mixture of acetonitrile and water or the like. Alternatively, the compound may be dissolved in a solvent such as acetone or acetonitrile and then the solution may be added with an appropriate amount of water to perform crystallization.

Figure 2:
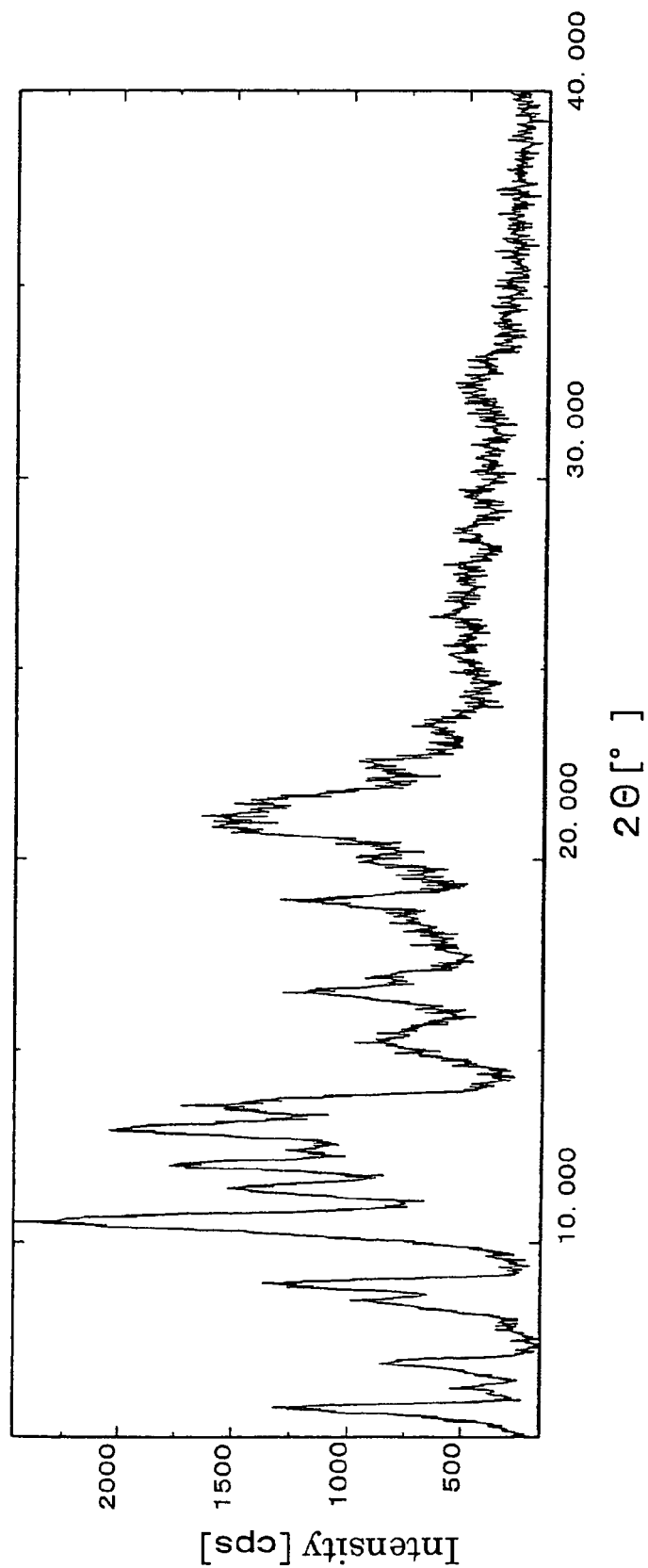
FIG. 2 shows a powder X-ray diffraction pattern of a mixture of a polymorphic crystal (α crystals), which is different from the crystal of the present invention, and the crystal of the present invention (β crystals).

An amount of the solvent used in the crystallization is not particularly limited. The amount is generally about 5 to 50 parts by weight, preferably about 20 to 25 parts by weight, based on the weight of the aforementioned compound. A temperature for crystallization is not particularly limited. The temperature is preferably, for example, in the range of from 0 to 45° C. A period for crystallization is generally from approximately 3 hours to 1 day. Crystals after the crystallization can be collected by filtration and then dried in a conventional manner to obtain the crystals of the present invention. When the crystals are dried, it is desirable that a temperature of the crystals is not rapidly lowered. The drying is preferably performed by air-drying or under reduced pressure with stirring at a temperature in the range of from room temperature to around 60° C. The drying is preferably performed at a temperature in the range of from 30 to 60° C. If the drying temperature is low, the crystals may be contaminated with crystals of other crystalline forms (α crystals). Whether the crystals of the present invention is obtained by the crystallization and drying steps is readily judged on the basis of information whether or not each diffraction angles of peaks of the resulting crystal in powder X-ray diffraction is identical to each of the aforementioned diffraction angles. FIG. 1 shows the X-ray diffraction patterns of the crystals of the present invention (β crystals) and FIG. 2 shows that of a mixture of α crystals and β crystals. The crystalline substance of the present invention has higher stability than that of an amorphous substance. For example, hygroscopicity of the crystalline substance of the present invention is lower than that of an amorphous substance as shown in the examples, which reveals excellent stability of the crystalline substance. In addition, superior stability of the crystalline substance of the present invention can also be confirmed by other techniques such as a light irradiation experiment.

Use of (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2- hydroxypropionate as an antitumor agent is described in detail in the international publication WO 01/27115, and the crystal of the present invention can be used as an active ingredient of the aforementioned antitumor agent. The entire disclosure of the international publication WO 01/27115 is incorporated herein by reference. By referring to the disclosure of the aforementioned international publication, those skilled in the art can use a medicament containing the crystal of the present invention as an active ingredient as an antitumor agent. The crystal of the present invention may also be used for the manufacture of the medicament containing the aforementioned compound as an active ingredient. For example, the crystal of the present invention may be used for the manufacture of injections or solutions provided in the form of a solution.

The medicament containing the crystal of the present invention as an active ingredient is preferably provided in the form of a pharmaceutical composition containing the crystal of the present invention as an active ingredient and one or more kinds of pharmaceutical additives. The administration route of the medicament of the present invention is not particularly limited, and the medicament can be administered orally or parenterally. (1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate, as the active ingredient of the medicament of the present invention, is characterized to exhibit antitumor effect even through oral administration. Accordingly, oral administration is a preferred administration route. Examples of pharmacologically and pharmaceutically acceptable additives used for manufacture of the aforementioned pharmaceutical composition include, but not limited to, excipients, disintegrating agents or disintegrating aids, binders, lubricants, coating agents, dyes, diluents, base materials, dissolving agents or dissolving aids, isotonic agents, pH modifiers, stabilizers, propellants, tackifier and the like.

Examples of preparation suitable for oral administration include, for example, tablets, powders, granules, capsules and the like. Examples of preparation suitable for parenteral administration include, for example, injections, fusion drips, suppositories, inhalants, patches and the like. Among them, capsules and tablets are preferred. For preparations suitable for oral administration, for example, excipients such as glucose, lactose, D-mannitol, starch and crystalline cellulose; disintegrating agents or disintegrating aids such as carboxymethylcellulose, starch and carboxymethylcellulose calcium; binders such as hydroxypropylcellulose, hydroxypropylmethylcellulose, polyvinylpyrrolidone and gelatin; lubricants such as magnesium stearate and talc; coating agents such as hydroxypropylmethylcellulose, saccharose, polyethylene glycol and titanium oxide; bases such as vaseline, liquid paraffin, polyethylene glycol, gelatin, kaolin, glycerin, purified water and hard fat can be used as the pharmacologically and pharmaceutically acceptable additives.

A dose of the medicament of the present invention is not particularly limited, and the dose can be suitably selected depending on various kinds of conditions such as the type of a tumor, the age, weight, symptom and the like of a patient and the like. The medicament is typically administered in an amount in the range of from about 0.5 mg to 50 mg, preferably about 1 mg to 20 mg, per 1 m² of body surface area.

EXAMPLES

Hereafter, the present invention will be more specifically explained by way of examples. However, the scope of the present invention is not limited to the following examples.

Example 1

(1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate (30.0 g, 34 mmol) was added with acetone (45 mL) and dissolved by stirring on a water bath at about 45° C. The solution was added dropwise with water (30 mL) of about 45° C. with stirring, and after completion of the addition, stirred for about 2 hours. Then, the water bath was cooled to about 23° C., and the solution was stirred overnight. The deposited crystals were collected by filtration and washed with a mixture of acetone and water (30 mL) having a water content of 60%. The crystals were dried under reduced pressure of about 600 mmHg at about 60° C. for 3 hours with stirring. Then, the crystals were dried under reduced pressure of about 150 mmHg for 1.5 hours and 30 mmHg for 1 hour to obtain 27 g (90%) of white crystals.

Figure 3:
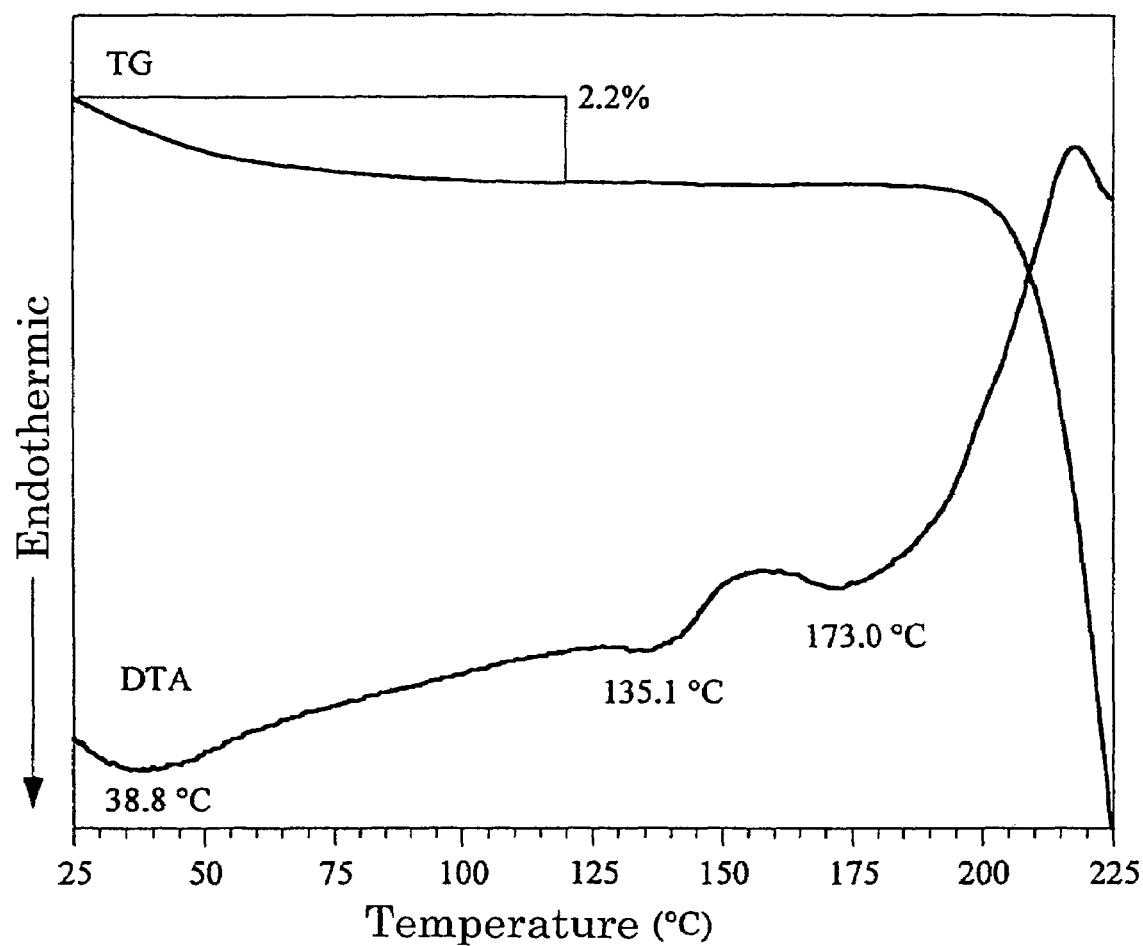
FIG. 3 shows a thermogravimetry/differential thermal analysis (TG/DTA) curve of the crystal of the present invention (β crystals).
Figure 4:
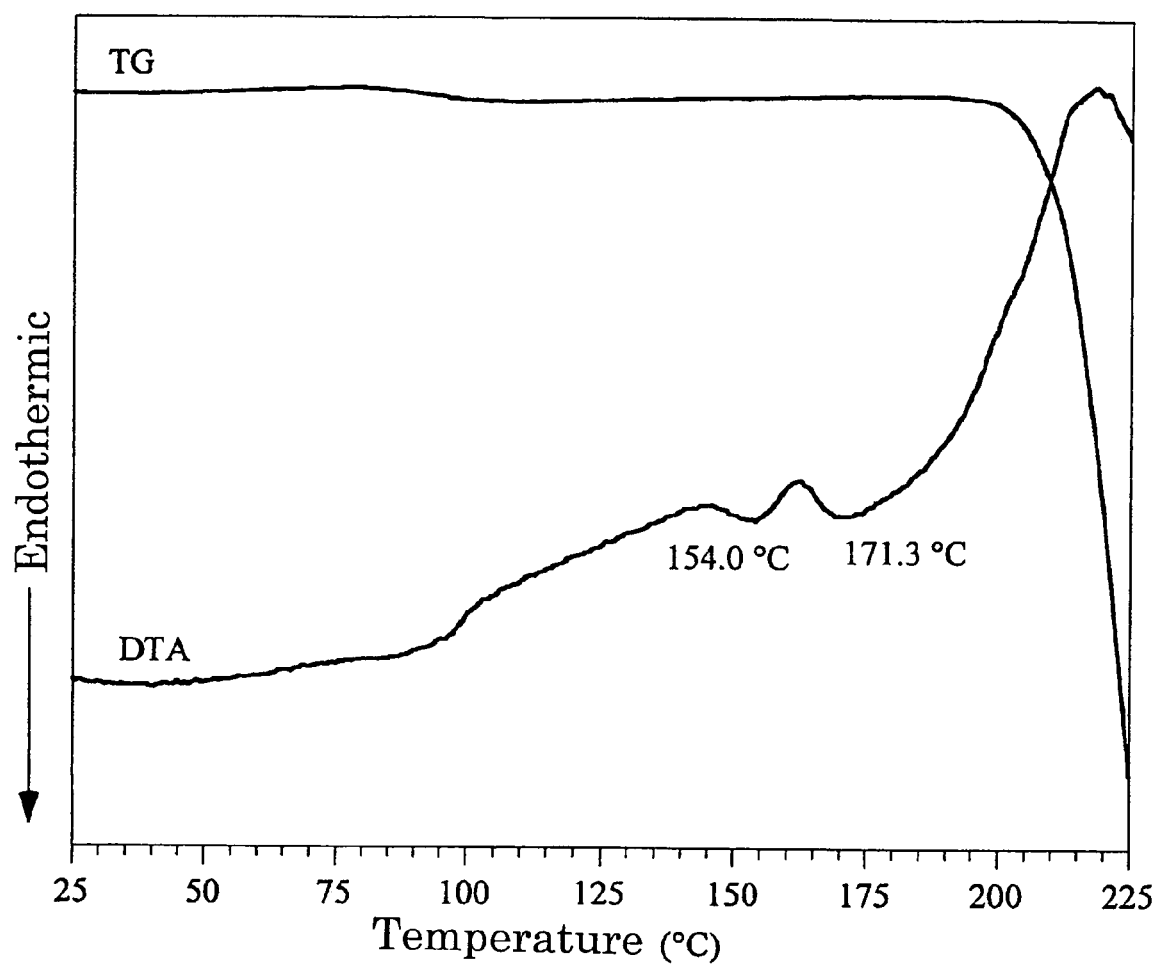
FIG. 4 shows a thermogravimetry/differential thermal analysis (TG/DTA) curve of a mixture of a polymorphic crystal (α crystals), which is different from the crystal of the present invention, and the crystal of the present invention (β crystals).
Figure 5:
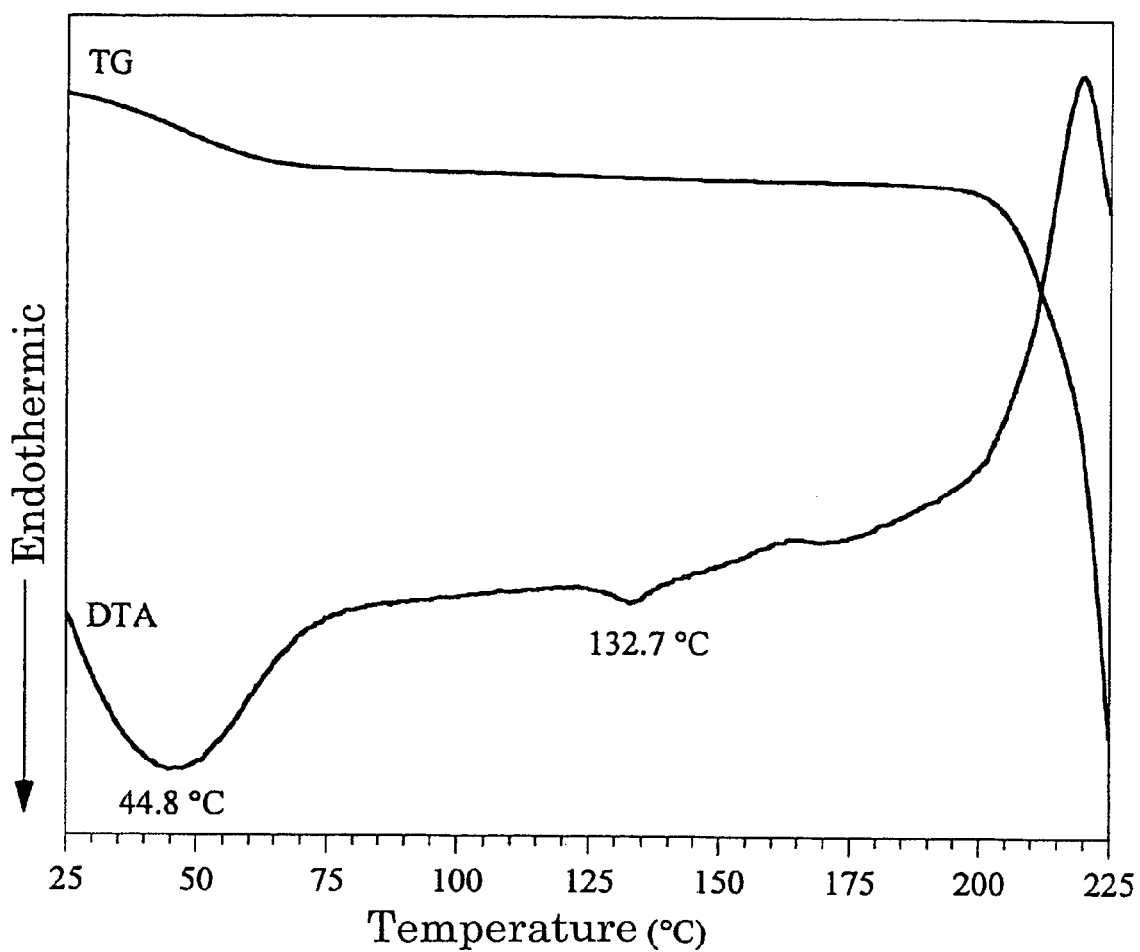
FIG. 5 shows a thermogravimetry/differential thermal analysis (TG/DTA) curve of an amorphous solid.

The resulting crystals were subjected to powder X-ray diffraction analysis. As a result, characteristic peaks were observed at diffraction angles (2 θ) of 6.18°, 10.30°, 10.68°, 11.38°, and 11.96°. The result of powder X-ray diffraction is shown in FIG. 1. Further, the results of thermogravimetric analysis and differential thermal analysis (TG/DTA) of the crystals are shown in FIG. 3.

Example 2

(1S,2S,3R,4S,5R,8R,9S,10R,13S)-4-Acetoxy-2-benzoyloxy-9,10-[(1S)-2-dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate (30.0 g, 34 mmol) was added with acetone (45 mL) and dissolved by stirring on a water bath at about 45° C. The solution was added dropwise with water (30 mL) of about 45° C. with stirring, and after completion of the addition, stirring was continued for about 2 hours. Then, the water bath was cooled to about 23° C., and the solution was stirred overnight. The deposited crystals were collected by filtration and washed with a mixture of acetone and water (30.0 mL) having a water content of 60%. The crystals were dried under reduced pressure of 60 mmHg at a temperature of 60° C. to obtain 27 g (90%) of white crystals. The resulting crystals were subjected to powder X-ray diffraction analysis. As a result, characteristic peaks similar to those of the crystals obtained in Example 1 were observed.

Example 3

(1S,2S,3R,4S,5R,8R,9S,10R,13S)-4-Acetoxy-2-benzoyloxy-9,10-[(1S)-2-dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate (2.5 g, 2.8 mmol) was added with acetone (38 mL) and dissolved by stirring on a water bath at about 45° C. The solution was added dropwise with water (25 mL) of about 45° C. with stirring, and after completion of the addition, stirring was continued for about 2 hours. Then, the water bath was cooled to about 23° C., and the solution was stirred overnight. The deposited crystals were collected by filtration and washed with a mixture of acetone and water (25 mL) having a water content of 60%. The crystals were air-dried at room temperature (about 19° C.) to obtain 2.3 g (92%) of white crystals. The resulting crystals were subjected to powder X-ray diffraction analysis. As a result, characteristic peaks similar to those of the crystals obtained in Example 1 were observed.

Example 4

(1S,2S,3R,4S,5R,8R,9S,10R,13S)-4-Acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate (2.5 g, 2.8 mmol) was added with acetonitrile (5 mL) and stirred on a water bath at about 45° C. The mixture was then added with water (3 mL) of about 45° C. and left stand at room temperature for 1 hour. The solution was further left stand at about 5° C. for 22 hours. The deposited crystals were collected by filtration and washed with cold acetonitrile:water (1:2, 5 mL). The crystals were dried under reduced pressure at 40° C. for 22 hours to obtain 0.37 g (74%) of white needle-like crystals. The resulting crystals were subjected to powder X-ray diffraction analysis. As a result, characteristic peaks similar to those of the crystals obtained in Example 1 were observed.

Example 5

Figure 6:
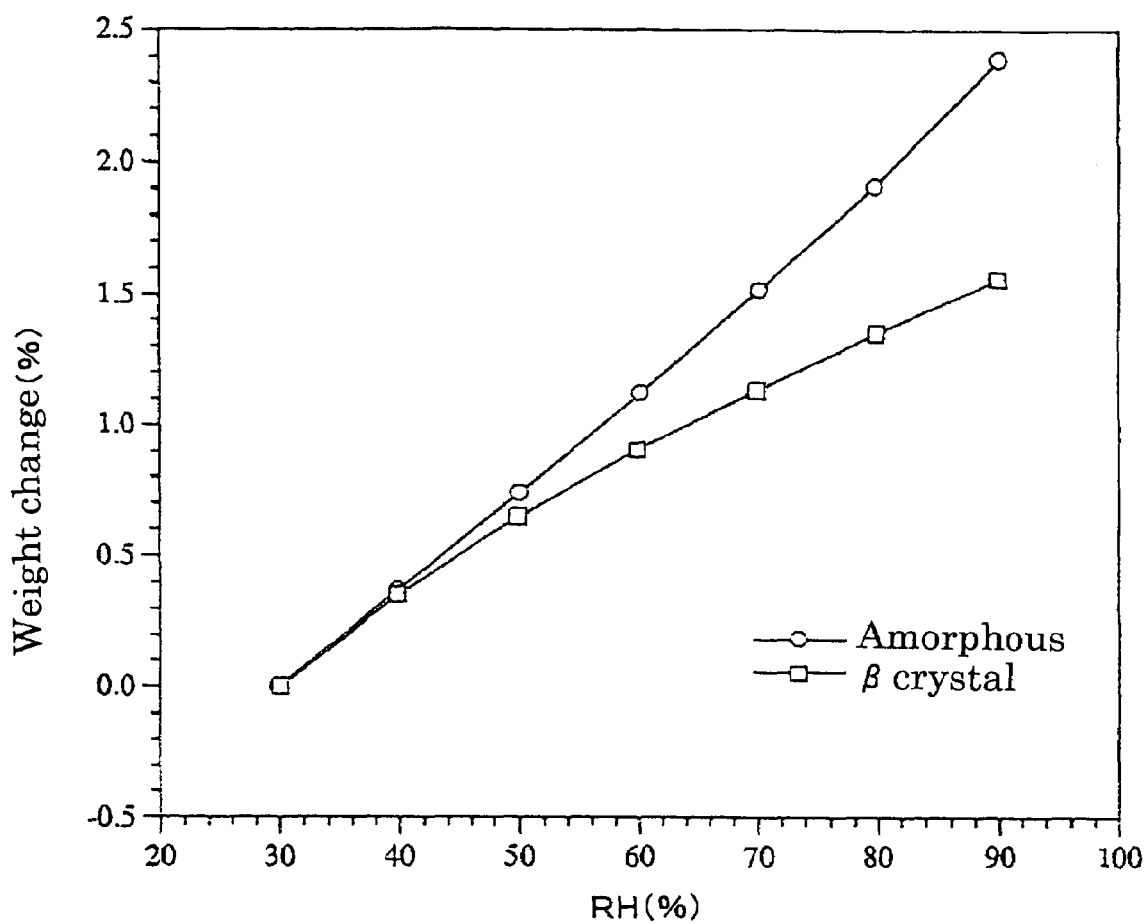
FIG. 6 shows results of measurement of moisture absorption behaviors of the crystals of the present invention (β crystals) and an amorphous substance measured at relative humidity of 30 to 90%.

Moisture absorption behaviors of the crystals of the present invention (β crystals) and an amorphous substance were measured under relative humidity of from 30 to 90%. Each sample of about 20 mg was used and the relative humidity was changed from 30% with 10% pitch by using a microbalance (automatic moisture adsorption apparatus). The measurement temperature was 25° C. An amount of the change was determined when the sample gave the change of 0.03% or less for 30 minutes (maximum retention time: 180 minutes). The results are shown in FIG. 6. The amorphous substance absorbed more moisture under high humidity by about 1% as compared to the crystals of the present invention.

INDUSTRIAL APPLICABILITY

A crystalline substance consisting of a single kind of crystal of the compound useful as an antitumor agent is provided by the present invention. By using the crystal of the present invention, a medicament having constant quality can be stably supplied.

What is claimed is:

1. A crystal of (1S,2S,3R,4S,5R,8R,9S,10R,13S)-4-acetoxy-2-benzoyloxy-9,10-[(1S)-2-(dimethylamino)ethylidenedioxy]-5,20-epoxy-1-hydroxytax-11-en-13-yl (2R,3S)-3-(tert-butoxycarbonylamino)-3-(3-fluoro-2-pyridyl)-2-hydroxypropionate, which has characteristic peaks at diffraction angles (2θ) of 6.2°, 10.3°, 10.7°, 11.4°, and 12.0° in a powder X-ray diffraction pattern.

2. A method for preparing the crystal according to claim 1, which comprises performing crystallization by using an organic solvent selected from the group consisting of a ketone type solvent, a nitrile type solvent, and a mixture thereof, or a mixture of said organic solvent and water.

3. The method according to claim 2, wherein the organic solvent is an organic solvent selected from the group consisting of acetone, acetonitrile, and a mixture thereof.

4. The method according to claim 2, wherein the crystallization is performed by using a mixture of acetone and water or a mixture of acetonitrile and water.

5. The method according to claim 4, wherein the mixture of acetone and water or the mixture of acetonitrile and water has a water content of 40 to 50% by weight.

6. The method according to claim 2, which comprises drying the crystals obtained by the crystallization at a temperature of from 30 to 60° C.

7. The method according to claim 3, which comprises drying the crystals obtained by the crystallization at a temperature of from 30 to 60° C.

8. The method according to claim 4, which comprises drying the crystals obtained by the crystallization at a temperature of from 30 to 60° C.

9. The method according to claim 5, which comprises drying the crystals obtained by the crystallization at a temperature of from 30 to 60° C.

* * * * *

UNITED STATES PATENT AND TRADEMARK OFFICE
CERTIFICATE OF CORRECTION

| | | |
|---|---|---|
| PATENT NO. | : 7,410,980 B2 | |
| APPLICATION NO. | : 10/495437 | |
| DATED | : August 12, 2008 | |
| INVENTOR(S) | : Uchida et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1188 days.

Signed and Sealed this

Twenty-sixth Day of October, 2010

David J. Kappos
*Director of the United States Patent and Trademark Office*